US012427255B2

(12) United States Patent
Naumburg et al.

(10) Patent No.: US 12,427,255 B2
(45) Date of Patent: Sep. 30, 2025

(54) INJECTION DEVICE FOR INJECTING A PHARMACEUTICAL SUBSTANCE, AND INJECTION LOADING PART FOR SUCH AN INJECTION DEVICE

(71) Applicant: Vetter Pharma-Fertigung GmbH & Co. KG, Ravensburg (DE)

(72) Inventors: Torsten Naumburg, Bad Waldsee-Untermöllenbronn (DE); Roland Limbeck, Biberach (DE)

(73) Assignee: Vetter Pharma-Fertigung GmbH & Co. KG, Ravensburg (DE)

( * ) Notice: Subject to any disclaimer, the term of this patent is extended or adjusted under 35 U.S.C. 154(b) by 727 days.

(21) Appl. No.: 17/843,207

(22) Filed: Jun. 17, 2022

(65) Prior Publication Data

US 2022/0313914 A1 Oct. 6, 2022

Related U.S. Application Data

(63) Continuation of application No. PCT/EP2020/086542, filed on Dec. 16, 2020.

(30) Foreign Application Priority Data

Dec. 19, 2019 (DE) .................. 102019220296.9

(51) Int. Cl.
*A61M 5/20* (2006.01)
*A61M 5/00* (2006.01)
*A61M 5/32* (2006.01)

(52) U.S. Cl.
CPC .......... *A61M 5/2033* (2013.01); *A61M 5/002* (2013.01); *A61M 5/326* (2013.01); *A61M 2005/2073* (2013.01)

(58) Field of Classification Search
CPC .... A61M 5/2033; A61M 5/022; A61M 5/326; A61M 2005/2073
See application file for complete search history.

(56) References Cited

U.S. PATENT DOCUMENTS

| 10,350,356 B2* | 7/2019 | Hirschel ............ A61M 5/3157 |
| 2012/0130318 A1 | 5/2012 | Young |
| 2015/0045729 A1* | 2/2015 | Denzer .................. A61J 1/065 |
| | | 604/110 |

FOREIGN PATENT DOCUMENTS

| DE | 102006041809 A1 | 3/2008 |
| EP | 2583704 A1 | 4/2013 |

(Continued)

OTHER PUBLICATIONS

International Search Report and Written Opinion for PCT/EP2020/086542 dated Apr. 8, 2021, 18 pages, English translation of ISR only.

*Primary Examiner* — Dung T Ulsh
(74) *Attorney, Agent, or Firm* — Sheppard Mullin Richter & Hampton LLP

(57) ABSTRACT

The invention relates to an injection device (1) for injecting a pharmaceutical substance, having
a proximal part (5) which has a drive (7) to implement an injection, and having
a distal part (13) which is configured to accommodate an injection loading part (3), which has a packaging means receiving part (17) and a primary packaging means (23) which held in the packaging means receiving part (17) and in which a pharmaceutical substance is received, wherein the pharmaceutical substance can be injected from the injection loading part (3) when the injection loading part (3) is arranged in the distal part (13), wherein (Continued)

the distal part (13) is designed in such a way that the injection loading part (3) can be inserted axially into the distal part (13), and wherein the injection device (1) has a screen (15) which is designed and arranged in such a way that an injection needle (25) of the injection loading part (3) is concealed from a user during use of the injection device (1).

17 Claims, 8 Drawing Sheets

(56) References Cited

FOREIGN PATENT DOCUMENTS

| EP | 2742962 A2 | 6/2014 |
| WO | 0117593 A1 | 3/2001 |
| WO | 2014146210 A1 | 9/2014 |

\* cited by examiner

INJECTION DEVICE FOR INJECTING A PHARMACEUTICAL SUBSTANCE, AND INJECTION LOADING PART FOR SUCH AN INJECTION DEVICE

CROSS-REFERENCE TO RELATED APPLICATION

This application is a continuation of International Application No. PCT/EP2020/086542, filed Dec. 16, 2020, which claims priority to German Patent Application No. 10 2019 220 296.9, filed on Dec. 19, 2019. The contents of each of the which are hereby incorporated by reference in their entirety into the present disclosure.

DESCRIPTION

The invention relates to an injection device for injecting a pharmaceutical substance, and to an injection loading part for use in such an injection device.

Injection devices of the type discussed here are used, in particular, for one-time or repeated injection of a pharmaceutical substance. In a particularly simple configuration as a conventional pen, they can have a drive device to which a cartridge can be attached in an exchangeable manner. An injection needle can in turn be connected to the cartridge. A piston can be displaced in the cartridge by the drive device in order to carry out an injection and expel the pharmaceutical substance via the injection needle. The injection needle is visible to a user when using the pen. This can lead to psychological and/or physical defensive reactions, and ultimately negatively affect compliance with a treatment plan. Such a pen can be reused by separating an empty cartridge from the drive device, and replacing it with a fresh cartridge. It is also possible for a pen to be provided for a single injection, wherein the entire pen, including the drive device, is disposed of after the injection. Such a pen is constructed integrally. It is therefore not adaptable to different primary packaging for pharmaceutical substances, and/or it has to be newly developed for each application. In addition, the use of such a disposable pen is expensive, and is therefore only considered for high-priced pharmaceutical substances. The BETACONNECT® produced by Bayer is a known injection device into which a specially designed syringe can be loaded. The injection device is reusable, and has a screen, such that an injection needle of the syringe loaded in the injection device is concealed from a user during use. The injection device is relatively complicated to use; in particular, the syringe must be inserted into the device by the same being opened, and the syringe being inserted from the side. In addition, this injection device, as noted, is configured for use with a specific type of syringe, and therefore cannot be used with other primary packaging materials.

The object of the invention is to create an injection device, and also an injection loading part for such an injection device, in which the named disadvantages do not occur.

The object is achieved by creating the present technical teaching—in particular, the teaching of the independent claims and of the embodiments disclosed in the dependent claims and the description.

The object is achieved in particular by creating an injection device that is configured for injecting a pharmaceutical substance. The injection device has a proximal part that has a drive that is configured to implement the injection. The injection device also has a distal part which is configured to receive an injection loading part, which has a packaging means receiving part and a primary packaging means held in the packaging means receiving part. A pharmaceutical substance is held in the primary packaging means, the pharmaceutical substance being injectable from the injection loading part when the injection loading part is arranged in the distal part. The distal part is designed in such a way that the injection loading part can be inserted axially into the distal part. The injection device has a screen which is designed and arranged in such a way that an injection needle of the injection loading part is concealed from a user during use of the injection device. With the proximal part and the distal part, the injection device has a simple and, in particular, clearly structured design: In particular, a functional separation is provided between the proximal part and the distal part, with the drive being provided in the proximal part and with the distal part serving to accommodate the injection loading part. As a result, in comparison to the proximal part, the distal part can be designed in a simple and cost-effective manner, which ultimately also reduces the overall complexity and the overall costs in the manufacture of the injection device. Depending on the specific design, a known proximal part, i.e., a drive device, of a conventional pen can also be used—supplemented by the distal part—so that the injection device can be provided particularly easily and with little refinement and/or production complexity. In addition, the injection device is easy to operate, and its function is also easy for the user to understand.

The fact that the distal part is configured to accommodate the injection loading part, which in turn accommodates the primary packaging means, means that the injection device can be easily adapted to different primary packaging means. All that is required is an adaptation of the injection loading part to the corresponding primary packaging means in such a manner that the primary packaging means can be accommodated in the injection loading part and the injection loading part can be accommodated in the distal part. The injection device can therefore be flexibly adapted to different applications.

In a preferred configuration, the injection device, in particular the distal part and the proximal part, is configured for repeated injection of a pharmaceutical substance, it being possible for it to be designed as a reusable injection device and in particular to be reloadable. In particular, the distal part and the proximal part are designed as parts that can be used multiple times. A used injection loading part can then be easily replaced with a fresh injection loading part. The injection loading part is preferably designed as a disposable part.

However, the injection device can also be used for a single injection of a pharmaceutical substance. In particular, it can then be disposed of together with a used injection loading part. Nevertheless, the advantage remains that, due to the multi-part structure with the proximal part, the distal part, and the injection loading part, a simple adaptation to different primary packaging means, and thus different application options, is possible.

The screen advantageously makes it possible for the user of the injection device to not see the injection needle, such that associated physical and/or psychological defense reactions are prevented. As a result, compliance associated with the use of the injection device is also high.

Advantageously, the screen is also a puncture protection, such that the injection needle remains concealed from the user not only visually but also haptically during the use of the injection device. This prevents unwanted prick injuries, apart from the actual injection to be carried out when using the injection device.

A screen means in particular a device or an element that is configured and arranged to conceal the injection needle in particular from view, but preferably also from unintentional contact by the user.

The fact that the injection needle is concealed from the user while the injection device is being used means, in particular, that the injection needle is concealed from view, and also preferably from undesired contact by the user, while the injection is being carried out, preferably while the injection loading part is being loaded into the distal part and during the injection, and particularly preferably also while the injection loading part is being removed.

In a preferred embodiment, the screen does not prevent the user from observing the progress of the injection or the fill level of the primary packaging. In particular, a viewing window is preferably formed in a peripheral wall of the distal part, through which the user can observe the progress of the injection and/or the filling level of the primary packaging means, in particular while an injection is being carried out.

A pharmaceutical substance is to be understood in particular as meaning a substance or mixture of substances which produces a pharmaceutical or medical effect and/or which is/are injected for a pharmaceutical and/or medical purpose. Such a pharmaceutical substance can in particular have at least one active substance and/or auxiliary substance, in particular at least one medicament.

Here, and in the following, "proximal" refers in particular to a direction in the coordinate system of the injection device and/or the injection loading part, which is intended to face away from an injection site at which an injection is to be carried out with the injection device. Correspondingly, "distal" designates a direction in the coordinate system of the injection device and/or the injection loading part which is intended to face the injection site. Correspondingly, the proximal part of the injection device faces away from the injection site during use as intended, and the distal part faces the injection site during use as intended.

The proximal part is in particular a back end of the injection device. In particular, this can also be a conventional back end of an injection pen, which is known per se.

The distal part is in particular a front end of the injection device.

The distal part is mechanically connectable or connected to the proximal part. In a preferred embodiment, it is possible for the distal part to be formed in one piece with the proximal part.

The drive is preferably designed as a mechanical drive or as an electrical drive. A mechanical drive is in particular a drive that can be operated manually by a user. The drive is preferably configured to implement the injection automatically, in particular as an electric drive. In a preferred embodiment, the proximal part has a control device that is configured to control the drive to implement the injection.

The fact that the drive is configured to implement the injection means in particular that activating the drive can cause the pharmaceutical substance to be expelled, and thus cause an injection.

The injection loading part is in particular a part that can be inserted into the distal part and preferably removed from the distal part, and that carries the primary packaging means and thus the pharmaceutical substance. In particular, it is preferably possible that the injection loading part can be exchangeably accommodated in the distal part.

The primary packaging means is configured in particular to hold the pharmaceutical substance directly in its interior. In particular, the primary packaging means is preferably designed as a syringe or as a cartridge. The primary packaging means preferably carries the injection needle—which is arranged in particular at a distal end of the primary packaging means, and can be connected to the primary packaging means in particular in a detachable or non-detachable manner.

The distal part preferably has a distinct direction of extension, its extension in the distinct direction of extension being longer than the extension in the two directions perpendicular to the distinct direction of extension. This distinct direction of extension is referred to as the axial direction. The distal part is thus designed to be elongate, in particular along the axial direction. The term "axial" refers in particular to this axial direction. A circumferential direction concentrically encompasses the axial direction. A radial direction is perpendicular to the axial direction.

The fact that the injection loading part can be inserted axially into the distal part preferably means in particular that it can be inserted into the distal part in the axial direction, in particular at the front, and can preferably likewise be removed from the distal part.

According to a refinement of the invention, it is provided that the drive of the proximal part is the only drive of the injection device. In particular, preferably no further drive is provided, regardless of a possible purpose of this further drive. The drive of the proximal part preferably acts on a piston rod of the injection device in order to displace the piston rod in the axial direction, in particular to expel the pharmaceutical substance from the injection loading part, and in order to move the piston rod back after the injection has been carried out, in the opposite direction. The injection device is preferably configured in such a way that at least one other mechanical function of the injection device is implemented by the displacement of the piston rod. The drive thus implements at least one additional functionality, in addition to actually driving the injection. This constitutes a particularly economical and simple configuration of the injection device.

The at least one further mechanical function is preferably selected from a group consisting of: inserting the injection needle into the injection site under the screen; locking the injection loading part and/or the screen, in particular in an injection position to implement the injection or in a rest position to prevent an unwanted injection; and unlocking the injection loading part and/or the screen, in particular to enable the injection needle to be inserted into the injection site.

According to a refinement of the invention, it is provided that the injection device is designed as a pen or as an auto-injector. The injection device is thus designed in a manner that is already known from other, conventional injection devices; their operation is known in general. A user will therefore have no major difficulties using the injection device. In particular, the injection device is configured for self-injection of the pharmaceutical substance by a patient, such that advantageously no medical specialist is required to use the injection device.

On the one hand, the further developments and preferred configurations disclosed below further refine the invention, independently of one another; on the other hand, they form a first preferred embodiment of the invention, preferably in combination with one another:

According to a refinement of the invention, it is provided that the distal part is detachably connected to the proximal part. In this way, the distal part and the proximal part can advantageously be handled and manipulated independently of one another. In particular, it is possible in this way to use a conventional backend for a conventional pen to provide the injection device, and to provide the injection device by connecting the backend, which is known per se, to the distal part configured according to the invention. In this case, the distal part can be connected to the back end—in particular, instead of a cartridge which is conventionally connected to the back end. However, it is of course also possible for the proximal part to be specially designed and provided for the injection device according to the invention.

If the distal part is detachably connected to the proximal part, it can in particular be separated from the distal part. Such a separation of the distal part from the proximal part can be provided in particular for introducing the injection loading part into the distal part and/or for maintenance or repair purposes.

The injection device preferably has a connection mechanism which is configured to detachably connect the distal part to the proximal part. According to a preferred embodiment, the connection mechanism can be designed as a plug-in/rotary connection, in particular as a bayonet lock.

Alternatively, however, it is also possible for the distal part to be permanently connected to the proximal part. The term "permanently" means in particular that the distal part cannot be separated from the proximal part without being destroyed, or at least not without the use of force.

According to a refinement of the invention, it is provided that the screen is provided or arranged rigidly on the distal part. In this case, the screen cannot be displaced relative to the distal part. The screen is preferably formed in one piece, preferably of the same material, with the distal part. In a particularly preferred embodiment, the screen is formed by the distal part. This means in particular that the distal part itself constitutes the screen at least in certain regions. In a particularly simple and functionally reliable manner, the injection needle remains concealed from the user's view through the distal part, with the distal part preferably also preventing the user from accidentally touching the injection needle. The distal part also serves as a puncture protection.

According to a refinement of the invention, it is provided that a proximal end face of the distal part has a loading opening through which the injection loading part can be inserted into the distal part. The loading opening is thus arranged and configured in such a way that it allows the injection loading part to be inserted into the distal part. The injection loading part is inserted into the distal part from a side which is remote from the injection site during intended use. In analogy to the conceptual description of firearms, the injection device according to this embodiment is designed as a breech loader.

In order to be able to insert the injection loading part into the distal part, the distal part is preferably detached from the proximal part so that the proximal end face of the distal part is accessible. In this configuration, the distal part is therefore preferably detachably connected to the proximal part.

According to a refinement of the invention, it is provided that a spring device is arranged in the distal part, against which the injection loading part rests, and against the spring force of which the injection loading part can be displaced in the distal part in the distal direction to carry out an injection when the injection loading part is arranged in the distal part. In order to carry out an injection, the injection loading part is thus displaced within the distal part and relative to the distal part in the direction of the injection site. In a preferred embodiment, to carry out the injection, a distal end face of the distal part is placed on the patient's skin in the region of the injection site, and the injection loading part is displaced within the distal part and relative to it in the distal direction, such that the injection needle penetrates the patient's skin and the injection can be carried out. The injection loading part is then pushed back again by the spring force of the spring device, such that the injection needle is also completely arranged inside the distal part once again. The distal part serves as a screen, preferably while simultaneously serving as a puncture protection.

The spring device is preferably supported by its distal end on a shoulder of the distal part, while the injection loading part lies against a proximal end of the spring device. In a preferred embodiment, the spring device is designed as a spring, in particular as a helical spring.

The displacement of the injection loading part within the distal part is preferably realized by the piston rod of the proximal part, and thus at the same time by its drive.

In particular, the injection loading part is displaceable in the distal part between a protection position in which the injection needle is arranged completely within the distal part, and an injection position in which the injection needle protrudes beyond the distal end face of the distal part and in which the injection is carried out. In order to carry out the injection, the injection loading part is displaced from the protection position in the axial direction against the spring force of the spring device into the injection position. After the injection has been carried out, in particular when the piston rod is pulled back, the spring device compels the injection loading part back out of the injection position into the protection position.

According to a refinement of the invention, it is provided that the injection device has a locking part that can be inserted into the distal part through the loading opening of the distal part, and that is configured to rest against a proximal contact surface of the injection loading part. The locking part has a base body and at least one locking element pivotably articulated on the base body. The locking part can be displaced within the distal part in particular between a first axial position, also referred to as the unlocking position, and a second axial position, also referred to as the locking position. In the first axial position, the locking part is arranged at a distance from a locking opening formed in a peripheral wall of the distal member. In the second axial position, the locking part is arranged at the level of the locking opening. When the locking part is arranged in the first axial position, the locking element is pivoted into the base body. If the locking part is arranged in the second axial position, the locking element can be pivoted out, and in particular can pass through the locking opening in order to block an axial displacement of the injection loading part relative to the distal part. This advantageously prevents the injection needle from penetrating too deeply into the patient's body, to the extent that this is not already prevented by the spring device—in particular, by the spring device moving against a limit stop; on the other hand, it also prevents the injection loading part from being pushed back too far in the direction of the protection position by the force of the spring device during the injection, as a result of which the injection needle would otherwise not penetrate deep enough into the patient's body or could slide out of the injection site entirely. Advantageously, the locking performed by the locking element thus preferably prevents an axial displacement of the injection loading part while the injection is being carried out, both in the distal and in the proximal direction. It is possible for the locking element and the locking opening to be matched to one another in such a way that there is a certain tolerance with regard to an axial displacement of the injection loading part within the distal part, wherein the locking opening provides stops—in particular, axial stops—for the locking element in both the proximal and the distal directions. A possible axial displacement of the injection loading part during the injection is thus limited by the locking opening.

The at least one locking element is preferably L-shaped. In particular, the L-shaped locking element has two legs which are connected to one another and are preferably formed in one piece and/or of the same material, wherein the L-shaped locking element is preferably articulated on the base body of the locking part in a connecting region of the two legs.

The locking part is preferably attached to the proximal part. Advantageously, it cannot fall off when the distal part is separated from the proximal part, in particular in order to insert the injection loading part into the distal part. However, it is also possible for the locking part to be present as a separate element. In this case, in order to insert an injection loading part into the distal part, the locking part is preferably manually removed from the distal part; the injection loading part is inserted into the distal part, and then the locking part is reinserted into the distal part, also via the proximal loading opening.

A plurality of locking elements is preferably articulated pivotably on the base body of the locking part. In a particularly preferred embodiment, there are two locking elements. The locking elements are preferably articulated on the base body uniformly—that is to say, at equal angular distances from one another as viewed in the circumferential direction. If two locking elements are provided, they are preferably diametrically opposed. In the peripheral wall of the distal part, there are preferably at least as many locking openings as the locking part has locking elements, preferably exactly as many, with the position of the locking openings viewed in the circumferential direction preferably being matched to the position of the locking elements, such that the locking elements can engage in the locking openings in the locking position. In a particularly preferred embodiment, two diametrically opposite locking openings are provided in the peripheral wall of the distal part.

According to a refinement of the invention, the locking part has an axial passage opening for the piston rod, the locking part being designed in such a way that the at least one locking element engages in the passage opening in the first axial position, such that the passage opening is blocked for the piston rod and the locking part can be displaced by the piston rod—in particular, together with the injection loading part, and thus at the same time together with the primary packaging means—wherein, in the second axial position, the locking element does not block the passage opening, such that the piston rod can pass through the passage opening and can be displaced relative to the locking part, in particular to displace a piston of the primary packaging means inside the primary packaging means and relative to the injection needle, such that the pharmaceutical substance is expelled from the primary packaging means. The locking element thus provides a limit stop for the piston rod in the release position, such that the piston rod can displace the locking part and the injection loading part together in the distal direction until the locking part reaches the second axial position and thus the locking position. The locking element can then pivot out, and in particular is pivoted by the piston rod in such a way that it passes through the locking opening, and at the same time releases the passage opening, such that the piston rod can pass through the locking part, moving past the locking element, and can act on the piston of the primary packaging means. In particular, in the release position, the L-shaped locking element engages in the passage opening with an inner leg of its two legs, such that the piston rod strikes the inner leg. If the locking part travels into the region of the locking opening, an outer limb of the two legs can pass through the locking opening, with the inner limb pivoting out of the passage opening and thus freeing the path for the piston rod through the passage opening. If the plunger rod is withdrawn from the passage opening after the injection has been completed, the locking part is pushed in the proximal direction by the force of the spring device, and the locking element is able to pivot back into the base body. It then no longer reaches through the locking opening, and the locking part can be displaced in the proximal direction together with the injection loading part.

This is where the refinements and preferred configurations that preferably form the first embodiment, in combination with one another, end.

On the one hand, the further developments and preferred configurations disclosed below further develop the invention independently of one another; on the other hand, they form a second preferred embodiment of the invention, preferably in combination with one another:

According to a further refinement of the invention, it is provided that the screen is held displaceably on the distal part. In particular, the screen is movable between a rest position and an exposed position. In the rest position, it conceals the injection needle, as long as no injection is being performed, while in the exposed position, it exposes the injection needle for the injection. The screen can be moved in particular in the axial direction. The screen preferably has a preferably radial projection on its outer peripheral surface. This radial projection strikes a distal end face of the distal part or an adjustable limit stop when at the most exposed position—i.e., at the greatest possible displacement in the proximal direction. In this way, the displacement of the screen in the proximal direction is advantageously limited.

The screen is preferably preloaded into the rest position, and is displaceable against the preload from the rest position into the exposed position. For this purpose, the distal part preferably has a preload device that is configured to preload the screen into the rest position. The preload device is preferably designed as a helical spring arranged in the distal part, which interacts with the screen and compels it into the rest position.

The screen is preferably displaced into the exposed position when the injection device is placed on a patient's body and pushed against the patient's body to perform an injection. At the same time as the screen is moved into the exposed position, the injection needle can penetrate the patient's body. The injection needle remains concealed from the user's view at all times, since the part of the injection needle that has not penetrated the patient's body is always covered by the screen.

In the configuration of the injection device in which the screen is held displaceably on the distal part, it is possible in particular for the distal part to be permanently connected to the proximal part, as explained above in connection with the first embodiment. However, it is also possible for the distal part to be detachable from the proximal part, in particular for repair or maintenance purposes, as is also explained above.

According to a refinement of the invention, it is provided that a distal end face of the distal part comprises the loading opening through which the injection loading part can be inserted into the distal part. In this case, the injection loading part is inserted into the distal part from the side which is intended to face an injection site. In this respect, the injection device is designed as a kind of muzzle loader. In particular, the injection loading part is preferably inserted through the screen into the distal part.

The injection loading part can preferably be turned, in particular screwed, into the distal part. For this purpose, the distal part on the one hand and the injection loading part on the other hand each have complementary screw threadings. Particularly preferably, at least one thread is formed in the distal part, in particular a right-hand thread. In a particularly simple configuration, a thread projection is arranged on the injection loading part, which is designed to interact with the thread in a form-fitting manner, and to be screwed into the thread. There is then no need for a separate formation of a thread on the injection loading part, allowing the construction thereof to be particularly simple. Two such threads are preferably arranged in the distal part, with the injection loading part correspondingly having two thread projections at the same time.

As an alternative or in addition, the injection loading part can preferably be arranged in an axially fixed manner in the distal part. A secure and stable axial position for the injection loading part in the distal part can thus be provided, with the injection loading part being held in the distal part, axially fixed relative thereto. In particular, the at least one thread can have a thread runout which defines the axial position of the injection loading part. Alternatively, it is possible for the distal part and the injection loading part to have a fixing mechanism, for example in the manner of a bayonet lock.

According to a refinement of the invention, it is provided that the distal part has a screen locking mechanism which is configured to block, and preferably lock, the screen in a blocking position against axial displacement, in particular against displacement between the rest position and the exposed position, and to permit the displacement of the screen when in a release position. Advantageously, the screen locking mechanism can prevent the screen from being inadvertently moved into the exposed position, thus exposing the injection needle when an injection is not being carried out. An unintentional viewing of the injection needle or—even worse—an unintentional prick injury by the injection needle, can be prevented in a particularly safe way.

The screen locking mechanism is preferably configured to be unblocked when the injection loading part is inserted, in particular when it is rotated into or screwed into the distal part. In particular, it is configured to be unblocked by inserting, in particular rotating in or screwing in, the injection loading part into the distal part. "Unblocked" means that the displacement of the screen from the rest position into the exposed position is permitted. Accordingly, in a simple manner and without additional effort for the user, the corresponding displacement of the screen can be enabled by inserting the injection loading part into the distal part as intended.

Alternatively or additionally, the screen locking mechanism is preferably configured to be blocked by the piston rod assigned to the drive. The screen can thus advantageously be locked once again, automatically, without further, additional intervention by the user when an injection is performed, or after an injection is performed. The screen locking mechanism is preferably blocked by the axial displacement of the piston rod in the distal direction, i.e., when the injection is carried out. This approach very reliably prevents an accidental prick injury after the injection is performed—a moment when typically the user's attention is lower than before the injection is performed.

According to a further refinement of the invention, it is provided that the screen locking mechanism has a rotary disk which is arranged in the distal part so that it can rotate about the longitudinal axis of the distal part between the locking position and the release position, the rotary disk having at least one recess passage, wherein the rotary disk with the at least one recess passage is configured and arranged in such a way that a blocking projection of the screen can be displaced through the recess passage in the release position, wherein the blocking projection, in the blocking position, strikes the rotary disk, in particular from the distal side. The rotary disk provides a simple and functionally reliable lock for the screen. If the rotary disk is arranged in the blocking position, the recess passage is in particular turned away from the blocking projection in such a way that it cannot be pushed through the recess passage, and therefore instead strikes the rotary disk, such that the screen cannot be displaced from the rest position into the exposed position. In the release position, on the other hand, the rotary disk with the at least one recess passage is pivoted in such a way that it exposes a displacement path for the blocking projection, such that the blocking projection can pass through the recess passage. The screen can then be displaced from the rest position into the exposed position, with the result that an injection can be carried out.

The passage recess is preferably designed as an open-edged recess in the rotary disk, in particular as a radial offset region on an outer circumference of the rotary disk.

The blocking projection is preferably ramp-shaped, sloping downward in the distal direction, and is arranged on a spring tongue or is part of the spring tongue. This has the advantage that the screen can also be displaced from the exposed position back into the rest position when the rotary disk is arranged in the blocking position. If, for example, the screen locking mechanism—in this case, the rotary disk—is displaced from the release position into the blocking position by the piston rod during its axial displacement, this typically occurs while the screen is still arranged in the exposed position. In particular, when the injection device is subsequently removed from a patient's skin, the screen is compelled from the exposed position back into the rest position. The blocking projection can then pivot radially outwards against a preload force of the spring tongue of which it is a part or on which it is arranged, and thus slide past the rotary disk, in particular an outer peripheral line of the rotary disk—in particular, due to its ramp-shaped configuration. Conversely, precisely because of the ramp-shaped or wedge-shaped design of the blocking projection, it cannot slide past the rotary disk in the blocking position if an attempt is made to move the screen from the rest position into the exposed position. In particular, the ramp-shaped design of the blocking projection on the spring tongue allows it to pass from the proximal side of the rotary disk to its distal side when the rotary disk is in the blocking position, but not in the opposite direction.

In the distal part, at least two latching positions are preferably provided for the rotary disk, with the rotary disk in particular engaging in one of the latching positions in the blocking position and in the other of the latching positions in the release position, and thus being held securely with regard to its angular position.

According to a further refinement of the invention, it is provided that the rotary disk has at least one driving surface which is designed to interact with a driver of the injection loading part, such that the rotary disk is rotated from the blocking position into the release position when the injection loading part is rotated in—in particular, screwed in, to the distal part will. This represents a simple and functionally reliable way of actuating the rotary disk with the injection loading part when the injection loading part is screwed in.

The at least one driving surface is preferably formed on a driving projection which extends on the rotary disk and extends, starting from an end face of the rotary disk, in the axial direction, in particular in the distal direction. The driver is designed in a complementary manner, preferably as a driving projection on the injection loading part, in particular on the functional sleeve, wherein it extends in particular starting from a distal end face of the injection loading part in the proximal direction.

Preferably, the driving surface and the driver together form a claw coupling.

The rotary disk preferably has two driving surfaces, in particular two driving projections, which are particularly preferably diametrically opposite one another. Correspondingly, the injection loading part preferably has two drivers, each of the drivers interacting with one driving surface of the rotary disk.

Alternatively or additionally, the rotary disk preferably has at least one runoff surface on which an actuating structure of the piston rod can move, such that the rotary disk is rotated from the release position into the blocking position when the piston rod is moved axially relative to the rotary disk in a specific direction, i.e., proximally or distally. In this way, the displacement of the rotary disk from the release position into the blocking position can be actuated by the piston rod in a simple and functionally reliable manner.

The actuating structure is preferably designed as an actuator projection or actuator pin, wherein the actuator projection or actuator pin extends radially outwards in the radial direction starting from an outer peripheral surface of the piston rod.

The rotary disk preferably has two such runoff surfaces, with the piston rod having two actuating structures, with each actuating structure interacting with one of the runoff surfaces. The runoff surfaces, and correspondingly the actuating structures, are preferably arranged diametrically opposite each other.

In particular, the at least one runoff surface is designed in such a way that the rotary disk is rotated when the piston rod with the actuating structure is axially displaced relative to the rotary disk in the distal direction, in particular when the actuating structure moves, in particular slides, in the distal direction along the runoff surface. This means in particular that the rotary disk is preferably rotated from the release position into the blocking position when an injection is effected by the piston rod and the pharmaceutical substance is expelled from the injection loading part.

A passage window is preferably arranged adjacent to the at least one runoff surface in the circumferential direction. The actuating structure can pass through this passage window in the event of a reverse axial displacement of the piston rod, without displacing the rotary disk. In particular, the actuating structure can pass through the passage window when the piston rod is axially displaced in the proximal direction relative to the rotary disk. A rotation of the rotary disk in the event of a reverse axial displacement of the piston rod, in particular a proximal displacement of the piston rod, is thus prevented. As such, in particular, the functions of locking on the one hand and unlocking on the other hand are separated with respect to the rotary disk: The rotary disk is unlocked when the injection loading part is screwed in—that is to say, it is rotated from the blocking position into the release position; it is locked, i.e., rotated from the release position into the blocking position, when the piston rod is axially displaced relative to the rotary disk in the specific direction, in particular in the distal direction.

According to a refinement of the invention, it is provided that the injection device, in particular the distal part, has an adjustable limit stop for the displaceable screen. The screen preferably strikes the adjustable limit stop in the exposed position. A penetration depth of the injection needle into the body of a patient can advantageously be adjusted, in particular prespecified, by means of the adjustable limit stop. If the adjustable limit stop is designed so that the screen hits the adjustable limit stop in the exposed position, the position of the screen can be changed directly relative to the distal part during the injection, which naturally alters the penetration depth of the injection needle.

This is where the refinements and preferred configurations that preferably form the second embodiment, in combination with one another, end.

The object is also achieved by creating an injection loading part which is configured for use in an injection device according to the invention, or in an injection device according to any of the embodiments described above. The injection loading part has a packaging means receiving part in which a primary packaging means is held, wherein a pharmaceutical substance is arranged in the primary packaging means. In particular, the injection loading part is designed to be accommodated in the distal part of the injection device. The advantages that have already been explained in the context of the injection loading part are in particular achieved with the injection device.

The injection loading part is preferably designed in the way that has already been explained explicitly or implicitly in connection with the injection device.

According to a further refinement of the invention, it is provided that the packaging receiving part has a functional sleeve and a retaining part, the primary packaging being accommodated in the functional sleeve and the primary packaging being secured, preferably fixed, in the functional sleeve by the retaining part. The functional sleeve is preferably designed to guide and hold the injection loading part in the distal part of the injection device. Alternatively or additionally—particularly in connection with the second embodiment—the functional sleeve is configured to unlock the screen locking mechanism. Alternatively or additionally, the functional sleeve is preferably configured to expose a needle protection part for manual removal when the injection loading part is or will be arranged in the distal part.

The fact that the primary packaging is received and secured in the functional sleeve means in particular that the primary packaging is held in the functional sleeve. This in turn means in particular that the primary packaging means cannot fall out of the functional sleeve or be unintentionally released from the functional sleeve or separated from the functional sleeve.

The retaining part is preferably designed as a clamping ring, a clip part, or a clip ring which is clamped or clipped to the functional sleeve when the primary packaging means is arranged in the functional sleeve, in order to secure, in particular to fix, the primary packaging means in the functional sleeve.

According to a refinement of the invention, it is provided that the injection loading part has a needle protection part that is detachably connected to the functional sleeve and that conceals an injection needle of the primary packaging means when the needle protection part is connected to the functional sleeve. This has the advantage that the injection needle is concealed even if the injection loading part is not arranged in the distal part of the injection device. In order to carry out an injection, the needle protection part must be detached from the functional sleeve, in particular it must be pulled off the functional sleeve.

The fact that the needle protection part is detachably connected to the functional sleeve means in particular that it is directly connected to the functional sleeve and/or that it is indirectly connected to the functional sleeve via the primary packaging means. It can also be connected directly to the primary packaging means. However, since the primary packaging means in turn is connected to the functional sleeve, the needle protection part is then also at least indirectly connected to the functional sleeve.

The fact that the needle protection part conceals the injection needle means, in particular, that it conceals it optically and haptically in such a way that a user does not see the injection needle, and accidental prick injuries by touching the injection needle are also prevented, since the injection needle is not accessible visually and haptically when the needle protection part is connected to the functional sleeve.

According to a refinement of the invention, it is provided that the needle protection part has an outer grip sleeve, and an elastic protective element which is arranged inside the grip sleeve in such a manner that it can move together therewith. The injection needle is accommodated in the elastic protective element when the needle protection part is connected to the functional sleeve. The protective element can in particular be made of or consist of pharmaceutical rubber or a similar material. A user can grip the needle protection part on the outer grip sleeve and pull it off the functional sleeve when they want to carry out an injection. The needle protection part with the outer grip sleeve preferably protrudes from the distal part and, in particular, also protrudes beyond the screen when the injection loading part is accommodated in the distal part, such that a user can easily grasp the outer grip sleeve of the needle protection part and pull the needle protection part off the functional sleeve.

The fact that the elastic protective element is arranged in the grip sleeve so that it can move together therewith means in particular that the elastic protective element is pulled off the injection needle when the outer grip sleeve is pulled off the functional sleeve. In particular, the elastic protective element is moved together with the grip sleeve.

According to a further refinement of the invention, it is provided that the injection loading part has at least one driver which is configured to interact with a driving surface of the rotary disk of the screen locking mechanism in such a way that the rotary disk is rotated from its blocking position into the release position when the injection loading part is inserted into the distal part. The driver is preferably designed as an axial projection on the injection loading part, in particular on the functional sleeve, which extends in the proximal direction. The injection loading part preferably has two such drivers. These two drivers are preferably formed diametrically opposite one another on the injection loading part.

According to a refinement of the invention, it is preferably provided that the needle protection part is locked on the functional sleeve in such a way that the needle protection part can only be separated from the functional sleeve when the injection loading part is arranged in the distal part. Advantageously, the needle protection part cannot then be inadvertently separated from the functional sleeve as long as the injection loading part is arranged outside of the distal part and therefore no injection is intended to be carried out. Prick injuries to a user can be prevented in particular very efficiently in this way.

The fact that the needle protection part is locked on the functional sleeve also means that, in a preferred embodiment, the needle protection part is clamped on the functional sleeve. A positive fit between the needle protection part and the functional sleeve is therefore not absolutely necessary. Nevertheless, such a positive fit can be provided.

The fact that the needle protection part can only be separated from the functional sleeve when the injection loading part is arranged in the distal part means in particular that the needle protection part can only be separated from the functional sleeve in a non-destructive manner—in particular, without the use of force—in that configuration.

The functional sleeve preferably has at least one spring arm which is elastically preloaded radially outwards, and preferably two spring arms which are elastically preloaded radially outwards, wherein the at least one spring arm holds the needle protection part. The at least one spring arm is compelled radially inwards against its preload and thus releases the needle protection part when the injection loading part is arranged in the distal part. In particular, the spring arm is then compelled radially inwards by an inner peripheral surface of the distal part.

The at least one spring arm is preferably designed as a clamping arm or locking arm.

At least one actuating lug is preferably arranged on the spring arm. This actuating lug then interacts with the distal part, such that the spring arm is compelled radially inwards against the preload when the injection loading part is arranged in the distal part.

The invention is explained in greater detail below with reference to the drawing. In the drawing.

Figure 1:
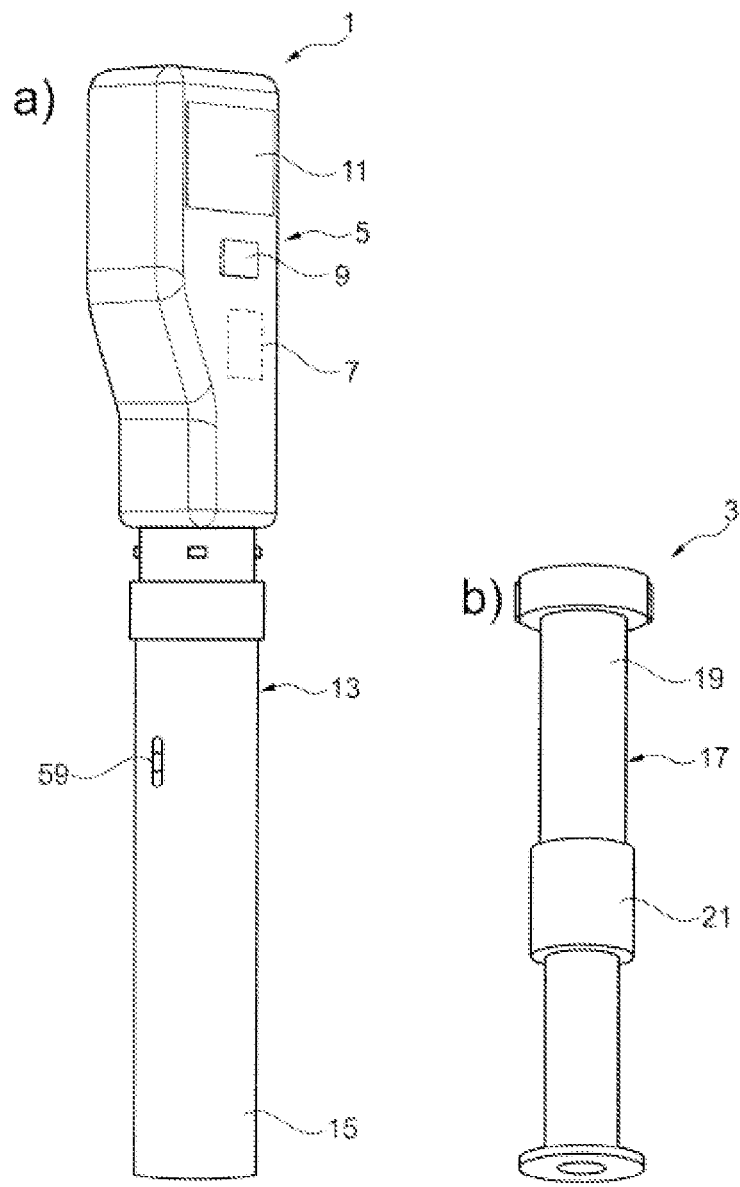
FIG. 1 is a first embodiment of an injection device and a first embodiment of an injection loading part for the injection device.

FIG. 1 shows a) a first embodiment of an injection device 1, and b) a first embodiment of an injection loading part 3 which is configured for use with the injection device 1, in particular for use in the injection device 1.

The injection device 1 is configured for injecting a pharmaceutical substance, and has a proximal part 5 which is also referred to as the back end. The proximal part 5 has a drive 7 which is located on the inside and which is configured to realize the injection. It is only indicated schematically here and is in particular not visible to the observer. The drive 7 can have an electric motor, for example, which acts on a piston rod (not shown in FIG. 1) in order to displace it axially. The drive 7 can be supplied with energy from an accumulator or a battery. It is possible for the drive 7 to be operatively connected to the piston rod via a gear.

The injection device 1 also preferably has a control device, which is likewise not shown in FIG. 1, and which is arranged in particular on the inner side of the proximal part 5. The control unit is configured to actuate the drive 7; in general, it is preferably configured to control the injection device 1 and to carry out an injection. It is possible for the control device to be connected to at least one sensor, in order to be able to carry out the injection as a function of at least one parameter detected by the sensor.

The proximal part 5 has an actuating button 9 which is in particular operatively connected to the control device and is preferably configured in such a way that the injection can be started and/or ended by actuating the actuating button 9.

Furthermore, the proximal part 5 preferably has a display device 11, in particular a display, which is preferably also connected to the control device and configured to display instructions to the user, in particular step-by-step instructions, parameter values, and/or the course of the injection.

It is possible for the proximal part 5 to be designed as a conventional back end of a conventional injection pen.

The injection device 1 also has a distal part 13, also referred to as a front end, which is configured to accommodate the injection loading part 3. The distal part 13 is designed in such a way that the injection loading part 3 can be inserted axially into the distal part 13.

An axial direction in this case is in particular a direction of the longest extension of the injection device 1, and preferably also of the distal part 13—in particular, a direction extending vertically in FIG. 1a). A circumferential direction concentrically encompasses the axial direction. A radial direction is perpendicular to the axial direction.

The injection device 1 also has a screen 15 which is designed and arranged in such a way that an injection needle (not shown in FIG. 1) of the injection loading part 3 is concealed from the user when the injection device 1 is being used. This makes the injection more pleasant, in particular psychologically. At the same time, puncture protection is preferably provided by the screen 15, which prevents the user from inadvertently injuring themself on the injection needle.

The term "distal" in this case refers to a direction on the injection device 1 intended to face an injection site, in particular the skin of a patient—that is to say, in FIG. 1a), in particular the lower end. The term "proximal", on the other hand, designates a direction on the injection device 1 which is away from the injection site—in FIG. 1a), accordingly, in particular the upper end of the injection device 1.

In the first embodiment, the distal part 13 is detachably connected to the proximal part 5. For this purpose, a connection mechanism is in particular provided, which can be designed, for example, in the manner of a bayonet lock.

The injection device 1 preferably has the drive 7 as the only drive. The injection device 1 is preferably configured in such a way that at least one other mechanical function of the injection device is implemented by the displacement of the piston rod—in particular, the puncture action of the injection needle under the screen 15, and/or a locking and/or unlocking of the injection loading part 3 and/or of the screen 15.

The injection device 1 is preferably designed as a pen or auto-injector.

The injection loading part 3 has a packaging means receiving part 17 in which a primary packaging means, that is hidden in FIG. 1b), is held. The pharmaceutical substance for the injection is arranged in the primary packaging means. The pharmaceutical substance can be injected out of the injection loading part 3 when the injection loading part 3 is arranged in the distal part 13.

The packaging receiving part 17 preferably has a functional sleeve 19 in which the primary packaging is received. In addition, the packaging receiving part 17 has a retaining part, not shown in FIG. 1, by means of which the primary packaging is secured—in particular, fixed—in the functional sleeve 19.

The injection loading part 3 has a needle protection part 21 which is detachably connected to the functional sleeve 19 and which conceals the injection needle of the primary packaging means when the needle protection part 21 is connected to the functional sleeve 19.

Figure 2:
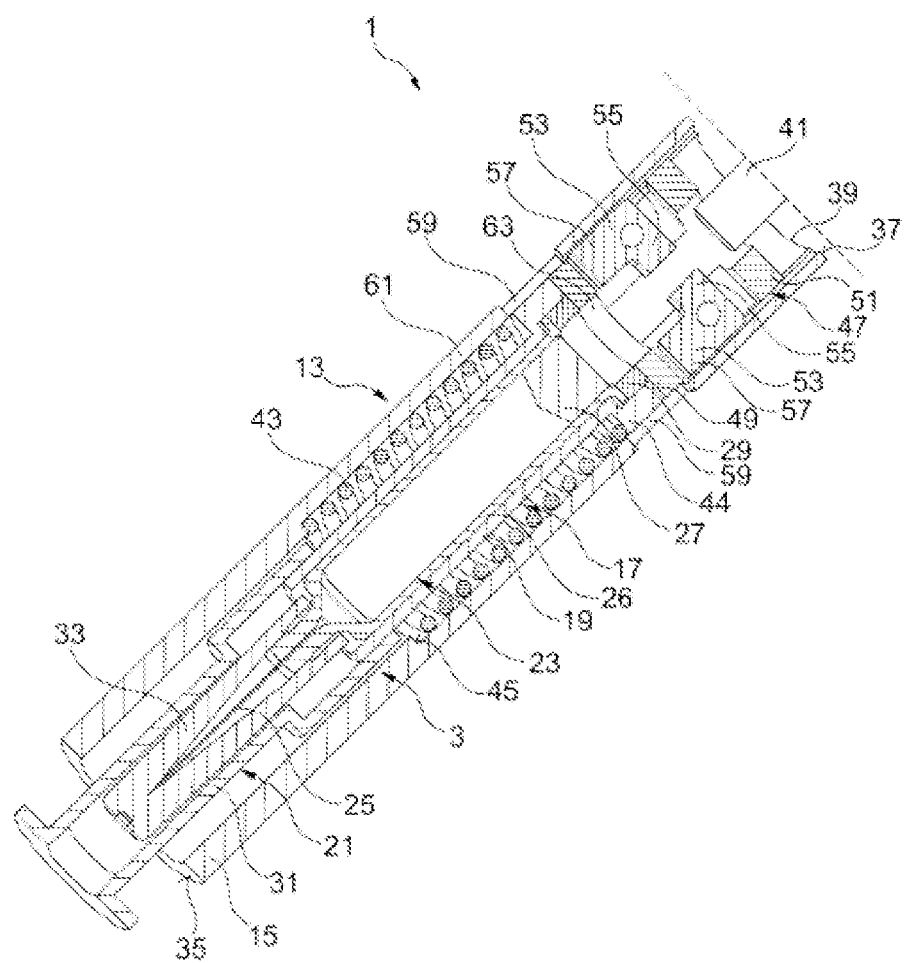
FIG. 2 is a detailed longitudinal sectional view of the injection device with the loading part according to FIG. 1, in a first functional position.

FIG. 2 is a detailed longitudinal sectional illustration of the first embodiment of the injection device 1, with the first embodiment of the injection loading part 3 according to FIG. 1, wherein the injection loading part 3 is accommodated in the distal part 13.

Identical and functionally identical elements are provided with the same reference symbols, such that in this respect reference is made to the preceding description.

In the sectional view of FIG. 2, a primary packaging means 23 accommodated in the functional sleeve 19 can be seen, which is designed in particular as a syringe or cartridge. The primary packaging 23 has an injection needle 25 which is fixed in this case to a packaging body 26 of the primary packaging 23, in particular glued to a distal end of the packaging body 26. A pharmaceutical substance (not shown) is arranged in the primary packaging means 23, as is a stopper or plunger 27 that can be displaced in the axial direction inside the primary packaging means 23. When it is displaced, the pharmaceutical substance can be expelled from the primary packaging means 23 in a manner known per se.

A retaining part 29, by means of which the primary packaging means 23 is held securely and stably in the functional sleeve 19, is connected to the functional sleeve 19 in this case. The retaining part 29 is preferably designed as a clamping ring, as a clip part, or as a clip ring.

The needle protection part 21 has an outer grip sleeve 31 and an elastic protective element 33, preferably made of pharmaceutical rubber, which is arranged inside the grip sleeve 31 in a manner allowing it to move together therewith. The injection needle 25 is accommodated in the elastic protective element 33 when the needle protection part 21 is connected to the functional sleeve 19. The user can grasp the needle protection part 21 on the outer grip sleeve 31 and pull it off the functional sleeve 19. At the same time, the elastic protective element 33 is moved with it and pulled off the injection needle 25. As a result, it is exposed, such that an injection is possible. The grip sleeve 31 protrudes, in particular in the distal direction, beyond a distal end face 35 of the distal part 13, so that it can be easily grasped and pulled off by the user. Even after the grip sleeve 31 and the elastic protective element 33 have been pulled off, the injection needle 25 is at least initially still arranged within the screen 15, and is therefore concealed from the user both visually and, preferably, haptically.

In the first embodiment, the screen 15 is rigid on the distal part 13. In particular, the screen 15 is formed by the distal part 13. The screen 15 is in this case in particular a part of a peripheral wall 61 of the distal part 13.

A proximal end face 37 of the distal part 13 has a loading opening 39 through which the injection loading part 3 can be inserted into the distal part 13. For this purpose, the user can first detach the distal part 13 from the proximal part 5, and then insert the injection loading part 3 into the distal part 13. Thereafter, the distal part 13 can be connected to the proximal part 5 again.

As can be seen in FIG. 2, when connected to the proximal part 5, a piston rod 41 of the proximal part 5, which can be displaced in the axial direction by the drive 7, also protrudes through the loading opening 39 into the distal part 13.

A spring device 43 is preferably arranged in the distal part 13, and is designed in this case as a helical spring. The injection loading part 3 is supported with a flange 44 on a proximal end of the spring device 43. The spring device 43 in turn is supported by its distal end on a shoulder 45 of the distal part 13. The injection loading part 3 is shown in FIG. 2 in a protection position. In the protection position, the injection needle 25 is arranged completely within the distal part 13 and thus in particular within the screen 15. The injection loading part 3 can be displaced within the distal part 13 against the spring force of the spring device 43 in the distal direction into an injection position. In the injection position, the injection needle 25 partially protrudes from the distal part 13, in particular beyond the distal end face 35. An injection can be carried out in this injection position. As will be explained below, the displacement of the injection loading part 3 in the distal part 13 is brought about by the piston rod 41.

The injection device 1 has a locking part 47 which can be inserted through the loading opening 39 into the distal part 13. The locking part 47 is designed to rest against a proximal contact surface 49 of the injection loading part 3. The locking part 47 has a base body 51 and at least one locking element 53 pivotably articulated on the base body 51—in the embodiment shown here, two diametrically opposite locking elements 53 pivotably articulated on the base body 51. The functionality of the locking part 47 in connection with the implementation of an injection is explained in more detail below with reference to FIGS. 3 and 4.

The locking part 47 can be attached to the proximal part 5 in such a manner that it can move together therewith, and at the same time can be displaceable relative to the proximal part 5 in such a way that the piston rod 41 can be displaced relative to the locking part 47 at the same time. This configuration has the advantage that the locking part 47 is easy to handle and cannot be lost. Alternatively, however, it is also possible for the locking part 47 to be designed as a separate element, which is inserted through the loading opening 39 in particular after the injection loading part 3 has been inserted into the distal part 13. It can then be removed again from the distal part 13 via the loading opening 39 in order to remove the injection loading part 3 after the injection has been carried out.

The locking elements 53 are L-shaped, with an inner leg 55 and an outer leg 57, the locking elements 53 being pivotably articulated on the base body 51 in the region of a connection or an intersection between the inner leg 55 and the outer leg 57. The inner leg 55 and the outer leg 57 are preferably perpendicular to one another.

The distal part 13 has at least one locking opening 59, in this case in particular two locking openings 59 diametrically opposite one another, which are designed in particular as windows in the peripheral wall 61 of the distal part 13. One of the locking openings 59 is also shown in FIG. 1a).

In FIG. 2, the locking part 47 is shown in a first axial position within the distal part 13, which is also referred to as the unlocking position, the locking part 47 being arranged at a distance from the locking openings 59 in the axial direction. In this first axial position and release position, the locking elements 53 are pivoted into the base body 51.

The locking part 47 has an axial passage opening 63 for the piston rod 41. The passage opening 63 passes through the base body 51 in such a way that the piston rod 41 can pass through the base body 51 through the passage opening 63, at least in a functional position of the locking part 47.

In the first axial position shown in FIG. 2, i.e., the release position, the inner legs 55 of the locking elements 53 in this case engage in the passage opening 63, such that the latter is blocked for the piston rod 41.

The locking part 47 can therefore be displaced—together with the injection loading part 3—by the piston rod 41, and is carried along by it when the piston rod 41 is displaced in the distal direction. At the same time, the primary packaging means 23 with the injection needle 25 is also displaced in the distal direction.

Figures 3, 4:
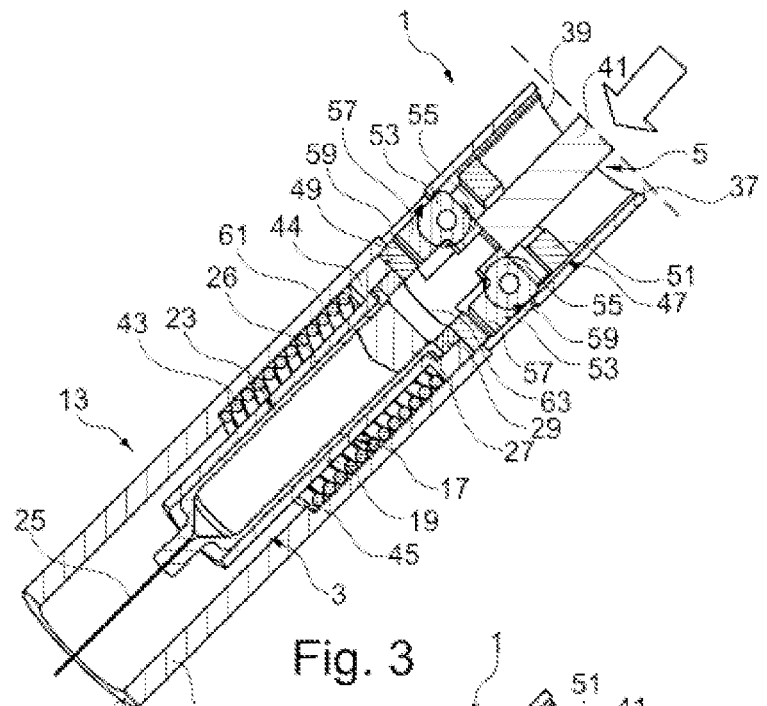
FIG. 3 is the injection device and the loading part according to FIG. 1, in a second functional position.
FIG. 4 is the injection device and the loading part according to FIG. 1, in a third functional position.

FIG. 3 shows the first embodiment of the injection device 1, with the injection loading part 3, with the needle protection part 21 removed, and in a functional position in which the locking part 47 has been displaced by the piston rod 41 from the first axial position in the direction of a second axial position, this second axial position also being referred to as the locked position. However, in FIG. 3, the locking part 47 has not yet reached the second axial position. However, it can be seen that the injection needle 25 already protrudes beyond the screen 15 and in particular the distal end face 35, and that the spring device 43 is compressed in comparison to FIG. 2. During the axial displacement of the locking part 47, the locking elements 53 move into the region of the locking openings 59. As shown in FIG. 3, they can pivot radially outwards in this region.

FIG. 4 shows the first embodiment of the injection device 3, with the injection loading part 3, in a further functional position, specifically in this case in the second axial position of the locking part 47—that is, in the locking position, with the injection loading part 3 now being arranged in the injection position at the same time. In the second axial position of the locking part 47, the locking elements 53 pivot out at the position of the locking openings 59, and pass through the locking openings 59—in particular, the outer legs 57 thereof pass through the same. At the same time, the locking elements 53 free the passage opening 63 for the passage of the piston rod 41, in particular by pivoting the inner legs 55 out of the passage opening 63 at least far enough for the piston rod 41 to pass between the inner legs 55. The piston rod 41 can thus also pass through the passage opening 63 and be displaced relative to the locking part 47. With the axial position of the injection loading part 3 fixed relative to the distal part 13, the piston rod 41 can now displace the piston 27 in the distal direction within the primary packaging means 23, relative thereto, and thus expel the pharmaceutical substance from the primary packaging means 23. In this way, in the injection position of the injection loading part 3, the injection is carried out.

An axial displacement of the injection loading part 3 relative to the distal part 13 is meanwhile blocked, or at least limited, by the locking elements 53 extending through the locking openings 59, both in the distal direction—provided that a further distal displacement of the injection loading part 3 is not already limited by the spring device 43, which has reached its maximum travel—as well as in the proximal direction, such that when the friction is reduced by the sliding of the plunger 27 in the primary packaging means 23, the injection loading part 3 cannot be pulled back within the distal part 13 against the spring force of the spring device 43, and thus possibly be retracted out of the patient's skin. A precise position of the locking elements 53 within the locking openings 59—in the axial direction—is determined in particular as a function of the sliding friction of the piston 27 in the primary packaging means 23, on the one hand, and the restoring force of the spring device 43 during the injection, on the other hand.

If the plunger rod 41 is pulled back in the proximal direction, particularly after the injection has been completed, and thereby disengages from the locking elements 53, the injection loading part 3 together with the locking part 47 is compelled in the proximal direction by the force of the spring device 43. The locking elements 53 now pivot back into the base body 51, and the injection loading part 3 is displaced back into its protection position by the spring device 43.

Figure 5:
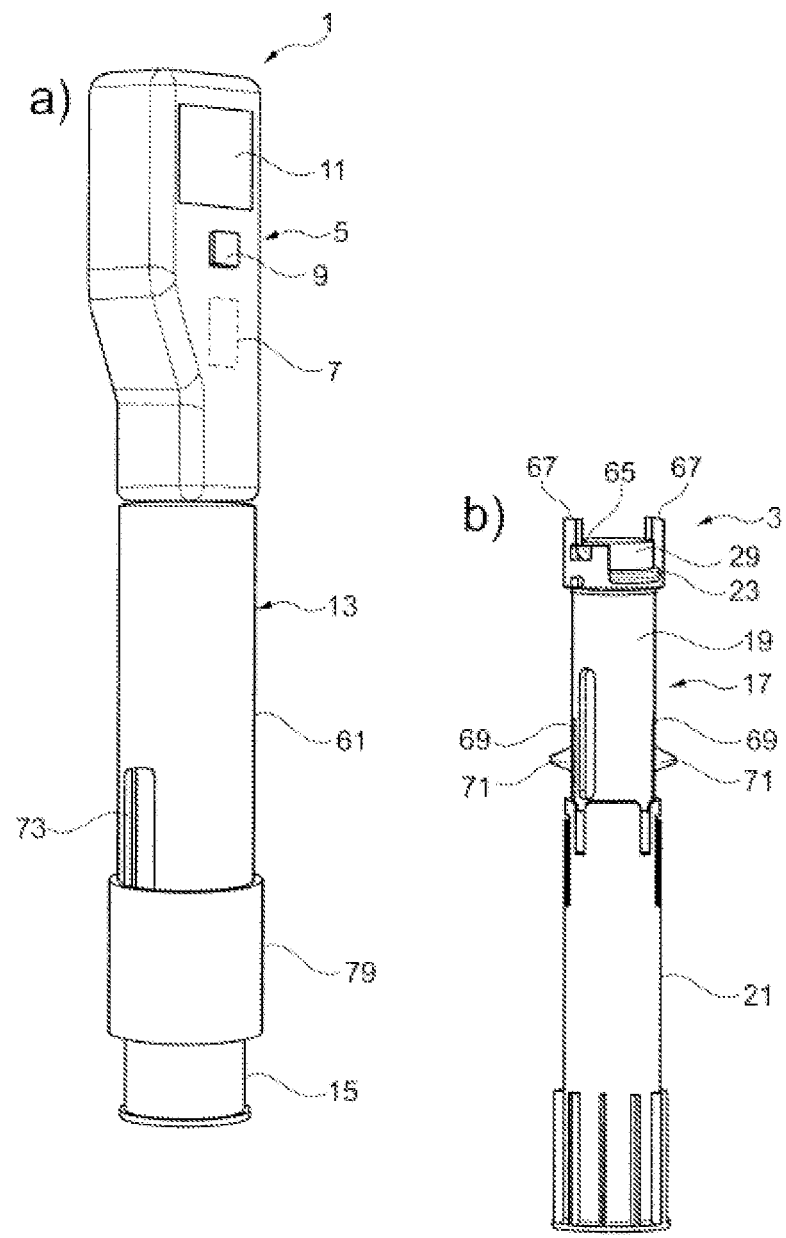
FIG. 5 is a second embodiment of an injection device and a second embodiment of an injection loading part.

FIG. 5 shows a) a second embodiment of an injection device 1, and b) a second embodiment of an injection loading part 3 which is configured to be used with the injection device 1, in particular in the injection device 1 according to the second embodiment.

In this second embodiment of the injection device 1, the screen 15 is held on the distal part 13 in a displaceable manner, in particular in an axially displaceable manner, in particular between a rest position and an exposed position. The screen 15 is shown in FIG. 5 in the rest position.

In this second embodiment of the injection device 1, the distal part 13 is preferably non-detachably connected to the proximal part 5. However, an embodiment is also possible in which the distal part 13 is detachably connected to the proximal part 5, for example for maintenance or repair purposes.

According to the second embodiment as well, the injection loading part 3 has, as in the first embodiment, the packaging receiving part 17 with the functional sleeve 19 and the retaining part 29. The latter is designed in this case as a clip ring and has, in particular, clip projections which engage in clip recesses 65—of which only one is visible to the viewer in this case, and therefore only one is shown—of the functional sleeve 19. The primary packaging means 23 is arranged in the functional sleeve 19 of the packaging means receiving part 17 and is secured there by the retaining part 29.

The injection loading part 3 according to the second embodiment has at least one driver 67, in this case two diametrically opposite drivers 67, the function of which will be explained below. The drivers 67 are designed in particular as proximal projections on the functional sleeve 19.

In the second embodiment, the needle protection part 21 is preferably locked on the functional sleeve 19 in such a way that the needle protection part 21 can only be separated from the functional sleeve 19, without destroying it, if the injection loading part 3 is arranged in the distal part 13. For this purpose, the functional sleeve 19 has in this case in particular at least one—in this case, two—spring arms 69, which are elastically preloaded radially outward, and which keep the needle protection part 21 locked. An actuating lug 71 is arranged on each of the spring arms 69. If the injection loading part 3 is inserted into the distal part 13, the actuating lugs 71 are pushed radially inwards by the peripheral wall 61 of the distal part 13, and the spring arms 69 release the needle protection part 21, such that it can be pulled off the functional sleeve 19.

Coming back to FIG. 5a), a viewing window 73 is preferably formed in the peripheral wall 61 of the distal part 13, through which the user can observe the progress of the injection and/or the filling level of the primary packaging means 23, in particular while an injection is being carried out.

Figure 6:
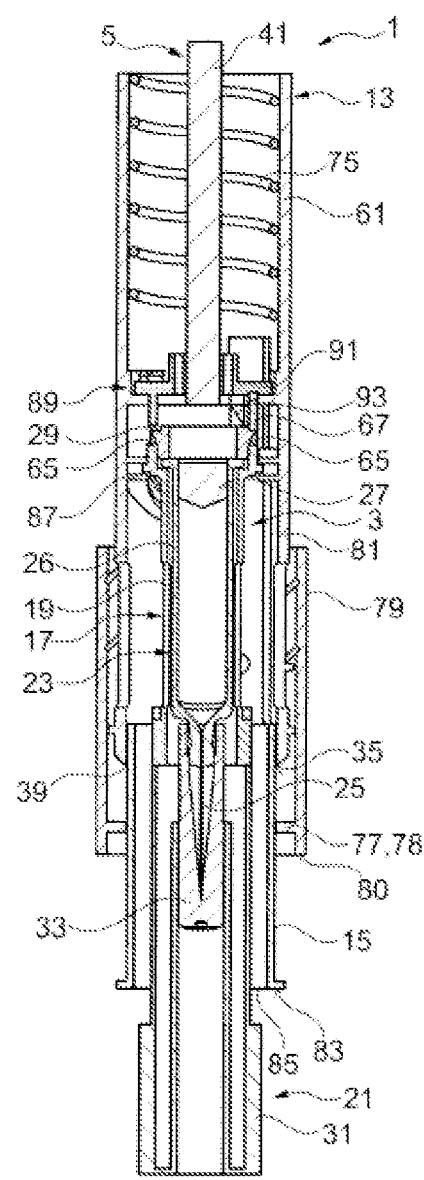
FIG. 6 is a detailed longitudinal sectional view of the injection device with the injection loading part according to FIG. 5.

FIG. 6 shows a detailed longitudinal section of the second embodiment of the injection device 3, with the injection loading part 3 accommodated in the distal part 13.

The illustration according to FIG. 6 shows that the screen 15 is preloaded into the rest position by a preload device 75. The preload device 75 is arranged in particular within the distal part 13, and is preferably designed as a helical spring. The screen 15 can be displaced axially and in the proximal direction against the preload of the preload device 75 from the rest position into the exposed position.

FIG. 6 also shows that the injection device 1 preferably has an adjustable limit stop 77 for the movable screen 15. The screen 15 preferably strikes the adjustable limit stop 77 in the exposed position. In particular, the distal part 13 has a stop sleeve 79 on its outer circumference, which has the limit stop 77 in particular as an inner radial projection, in particular as an inner annular collar 78, or as an outer annular collar, or simply as a distal end face 80, wherein the screen 15 strikes the limit stop 77, in the exposed position, by a radially-outer annular collar thereof. The limit stop 77 does not have to have a flat shape—in particular at least one stop point can also be provided. An axial position of the stop sleeve 79 relative to a sleeve body 81 of the distal part 13 can be changed, wherein the axial position of the limit stop 77 is changed at the same time. For this purpose, the stop sleeve 79, on the one hand, and the sleeve body 81, on the other hand, preferably have complementary, meshing threaded parts, in particular the sleeve body 81 has an external thread and the stop sleeve 79 has a corresponding internal thread. The threaded parts preferably form a self-locking thread with one another. Moving the stop sleeve 79 accordingly changes the position of the screen 15 relative to the distal part 13 in the exposed position during the injection, and thus also the depth of penetration of the injection needle 25 into the patient's body.

In the second embodiment of the injection device 1, the distal end face 35 of the distal part 13 has the loading opening 39 through which the injection loading part 3 can be inserted into the distal part 13. In particular, a distal end surface 83 of the screen 15 has a corresponding screen loading opening 85 through which the injection loading part 3 can be inserted into the interior of the distal part 13. The injection loading part 3 is thus inserted into the distal part 13 in particular through the screen 15. In this case, the injection loading part 3 can preferably be rotated, and in particular, screwed, into the distal part 13. For this purpose, the distal part 13 preferably has a screw means, in particular at least one thread 87, in which the injection loading part 3 preferably engages with at least one thread projection, preferably with two thread projections—one on each side—such that the injection loading part 3 can be screwed into the at least one thread 87.

The injection loading part 3 can preferably be arranged in an axially fixed manner in the distal part 13. For this purpose, the at least one thread 87 can in particular have a thread runout.

The distal part 13 has a screen locking mechanism 89 which, in a locking position of the screen locking mechanism 89, is arranged to block the screen 15, i.e., to lock it, against axial displacement between the rest position and the exposed position, and, in a release position, to permit this displacement. The screen locking mechanism 89 is preferably configured to be unblocked when the injection loading part 3 is being inserted into—in particular, rotated into or screwed into—the distal part 13, and to be blocked by the piston rod 41, in particular during its axial displacement, in particular in the distal direction. For this purpose, the screen displacement mechanism 89 preferably has a rotary disk 91 which is arranged in the distal part 13 so that it can rotate between the blocking position and the release position about a longitudinal axis of the distal part 13, which is vertical in FIG. 6. In the release position, a blocking projection 93 of the screen 15 can be displaced from the distal side of the rotary disk 91 to its proximal side, with the blocking projection 93 striking the distal side of the rotary disk 91 in the blocking position. A displaced of the screen 15 into the exposed position is then blocked.

Figure 7:
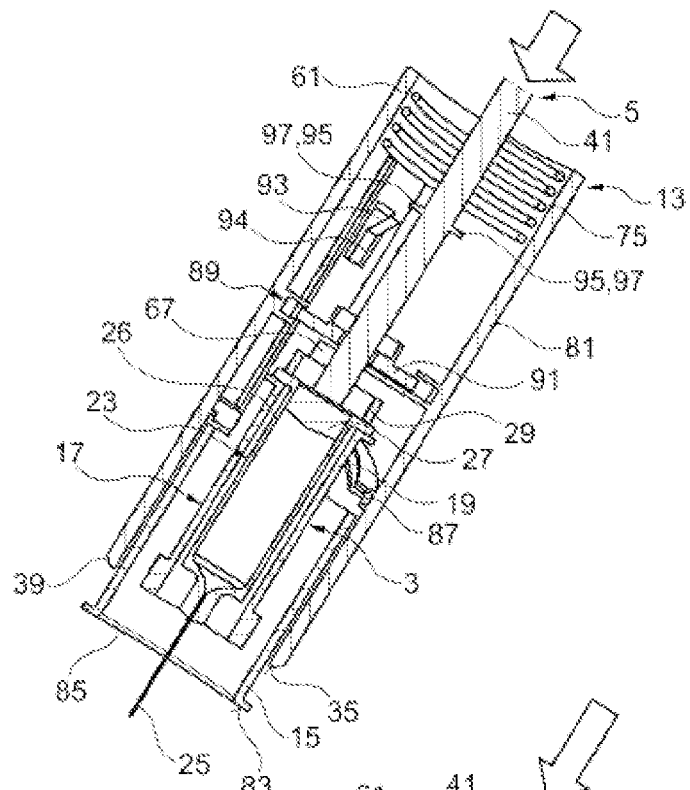
FIG. 7 is a detailed longitudinal sectional view of the injection device with the injection loading part according to FIG. 5, in a first functional position.

FIG. 7 shows a further detailed longitudinal section of the second embodiment of the injection device 1, with the injection loading part 3 in a first functional position, in this case specifically the release position of the screen locking mechanism 89. By rotating or screwing the injection loading part 3 into the distal part 13, the rotary disk 91 has been rotated into the release position, such that the screen 15 is displaced with its blocking projection 93 in the proximal direction against the preload force of the preload device 75, into the exposed position. In comparison to FIG. 6, the blocking projection 93 is now no longer arranged on the distal side of the rotary disk 91, but rather on its proximal side. The injection needle 25 is thus uncovered, such that an injection can be carried out by displacing the piston rod 41 distally. It should be noted that in the second embodiment, the injection loading part 3 is not displaced in the axial direction for the purpose of performing the injection.

Figure 8:
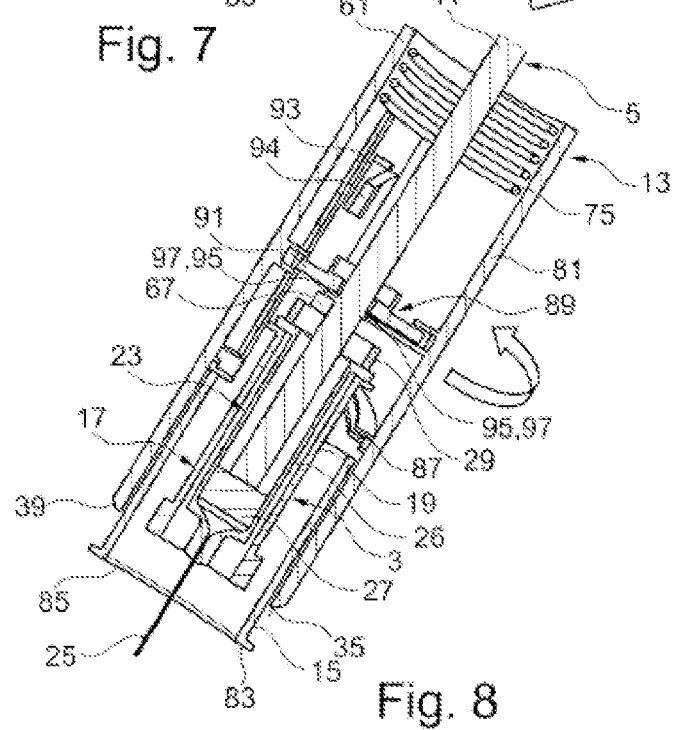
FIG. 8 is the injection device and the injection loading part according to FIG. 5, in a second functional position.

FIG. 8 shows an illustration of the second embodiment of the injection device 1, corresponding to the illustration in FIG. 7, with the injection loading part 3 in a second functional position. The figure shows that a displacement of the piston rod 41 in the axial direction, for carrying out the injection, causes the rotary disk 91 to be rotated into the blocking position by the piston rod 41. As such, the piston rod 41 has an actuating structure 95, in this case in the form of two actuator pins 97, with the actuating structure 95 rotating the rotary disk 91 in the direction of its blocking position when the actuating structure 95 passes the rotary disk coming from the proximal side in the direction of the distal side.

In contrast, there is no further rotation of the rotary disk 91 when the piston rod 41, and in particular the actuating structure 95, are moved back from the distal side to the proximal side of the rotary disk 91. After the end of the injection, the needle protection part 15 can nevertheless return from the exposed position to its rest position, driven by the preload force of the preload device 75, since the blocking projection 93 is arranged on a spring tongue 94 and is designed in the form of a ramp, such that it deflects radially outwards when it comes into contact with the rotary disk 91—and accordingly, the rotary disk 91 can pass to the distal side coming from the proximal direction.

Figure 9:
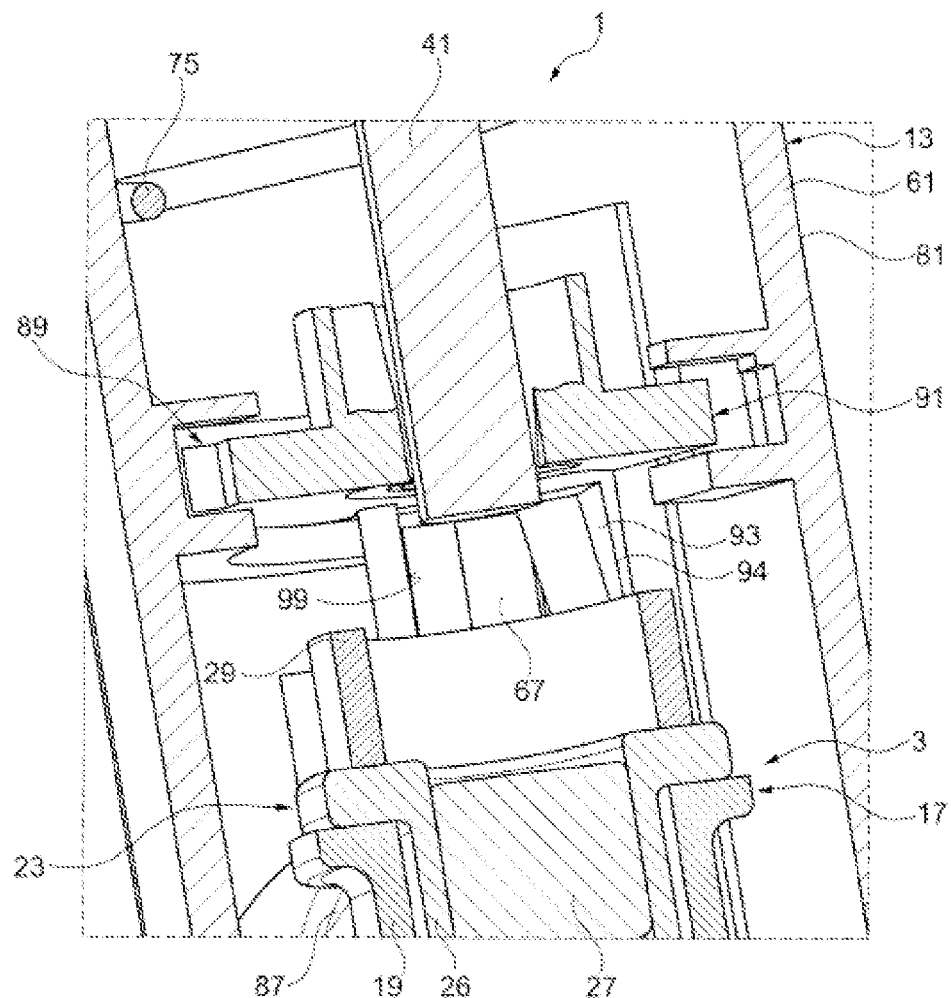
FIG. 9 is a further detailed longitudinal sectional view of the injection device and the injection loading part according to FIG. 5.

FIG. 9 shows a further detailed illustration of the second embodiment of the injection device 1, with the injection loading part 3. This illustration makes it clear that the rotary disk 91 has at least one driving surface 99, preferably two driving surfaces 99, in particular diametrically opposite one another, wherein the driving surface 99 is configured to work together with one of the drivers 67 of the injection loading part 3 in such a way that the rotary disk 91 is rotated from the blocking position into the release position when the injection loading part 3 is screwed into the distal part 13. The driving surface 99 is arranged in particular on a driving projection which extends in the distal direction on the rotary disk 91. In particular, the driver 67 and the driving surface 99 preferably work together in the manner of a claw coupling.

Figure 10:
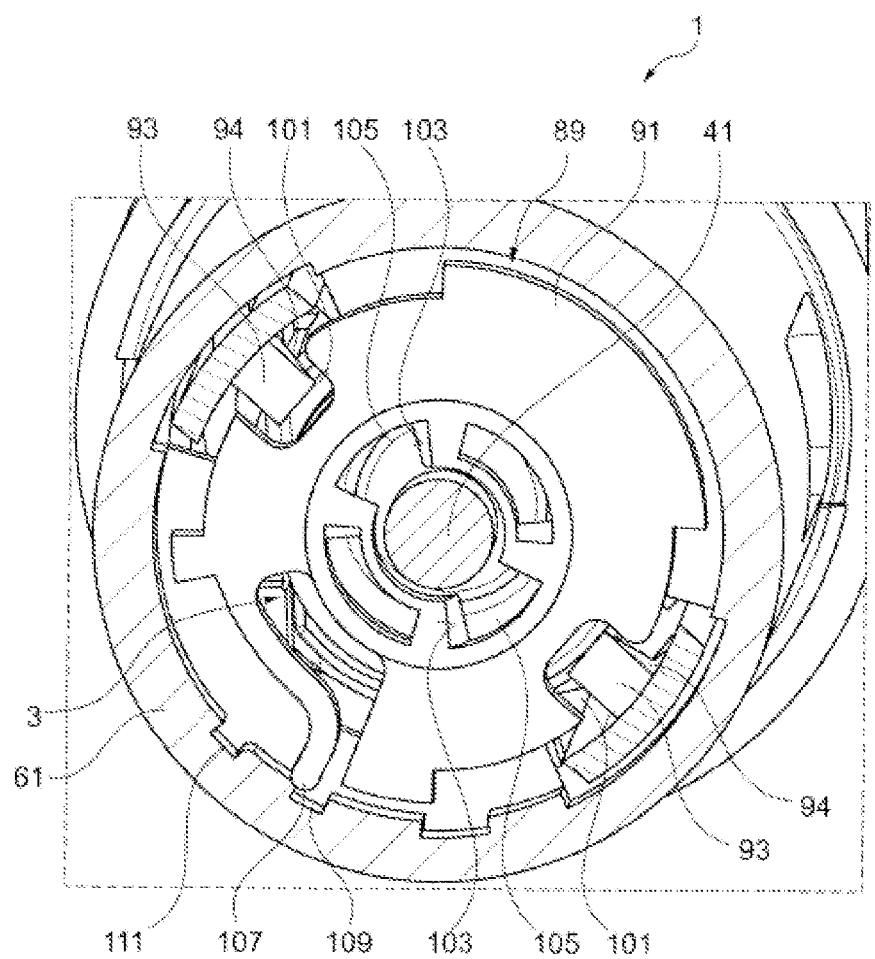
FIG. 10 is a detailed cross-sectional view of the injection device and the injection loading part according to FIG. 5.

FIG. 10 is a detailed cross-sectional illustration of the second embodiment of the injection device 1, with the injection loading part 3, wherein the cross-sectional plane in this case is arranged just above, i.e., proximal to, the rotary disk 91.

In this illustration, it is clear that the rotary disk 91 has at least one recess passage 101, in this case in particular two diametrically opposite recess passages 101, through which, in the release position which is shown in FIG. 10, the blocking projection 93 of the screen 15—in this case, two diametrically opposite blocking projections 93—can be displaced. The recess passages 101 are designed in particular as radial, open-edged cutouts.

In addition, it is clear from the illustration in FIG. 10 that the rotary disk 91 preferably has at least one runoff surface 103—in this case, in particular two, preferably diametrically opposite, runoff surfaces 103—wherein the actuating structure 95, in particular the actuator pins 97, of the piston rod 41 can move off the runoff surfaces 103 when the piston rod 41 is displaced in the distal direction. The rotary disk 91 is rotated from the release position into the blocking position when the piston rod 41 is displaced axially in the distal direction relative to the rotary disk 91, in particular when the actuating structure 95, in particular the actuator pins 97, passes the rotary disk coming from the proximal side in the direction of the distal side.

In this case, the injection loading part 3 is preferably also turned back by the corresponding angle in the thread runout; However, due to the design of the thread runout of the at least one thread 87, preferably no, or at most a slight, axial displacement of the injection loading part 3 relative to the distal part 13 results. A rotation of the injection needle 25 in the patient's body is preferably at least largely avoided, because the primary packaging means 23 is preferably accommodated in the functional sleeve 19 in a freely rotatable manner.

Adjacent to the runoff surfaces 103 in the circumferential direction, passage windows 105 are formed, through which the actuating structure 95 can be displaced from the distal side back to the proximal side—preferably without contacting the rotary disk 91—when the piston rod 41 is pulled back. As such, the rotary disk 91 does not rotate when the piston rod 41 is pulled back in the proximal direction after the injection has been performed.

FIG. 10 also shows that the rotary disk 91 preferably has a latching lug 107 with which it can latch into corresponding latching recesses 109, 111 in the peripheral wall 61 of the distal part 13, on the one hand in the release position, and on the other hand in the blocking position. A first latching recess 109 is functionally assigned to the release position shown in FIG. 10. A second locking recess 111 is functionally assigned to the blocking position. In particular, the latching recess 109, and the latching of the latching lug 107 therein, also serve in particular to provide mechanical/haptic—and possibly also acoustic—feedback to the user that the injection loading part 3 is entirely arranged in the distal part 13—that is, it is ready for injection.

It is thus also clear that, viewed in the viewer's direction from FIG. 10, the rotary disk 13 is rotated counterclockwise from the blocking position into the release position when the injection loading part 3 is screwed in, whereas it is rotated clockwise from the release position back into the blocking position when the actuating structure 95 moves off the runoff surfaces 103.

The invention claimed is:
1. An injection device (1), comprising
a proximal part (5) which has a drive (7) to implement an injection, and having
a distal part (13) which is configured to accommodate an injection loading part (3), which has a packaging means receiving part (17) and a primary packaging means (23) which held in the packaging means receiving part (17) and in which a pharmaceutical substance is received, wherein the pharmaceutical substance can be injected from the injection loading part (3) when the injection loading part (3) is arranged in the distal part (13), wherein
the distal part (13) is designed in such a way that the injection loading part (3) can be inserted axially into the distal part (13), wherein
the injection device (1) has a screen (15) which is designed and arranged in such a way that an injection needle (25) of the injection loading part (3) is concealed from a user during use of the injection device (1), wherein
a proximal end face (37) of the distal part (13) has a loading opening (39) through which
the injection loading part (3) can be inserted into the distal part (13), and wherein the injection device has a locking part (47) which can be inserted through the loading opening (39) into the distal part (13) and which is configured to contact a proximal contact surface (49) of the injection loading part (3), the locking part (47) having a base body (51) and at least one locking element (53) which is pivotably articulated on the base body (51) and which, in a first axial position inside the distal part (13), remote from a locking opening (59) which is formed in a peripheral wall (61) of the distal part (13), is pivoted into the base body (51), wherein the locking element (53) is configured to pivot out, in a second axial position inside the distal part (13), at the position of the locking opening (59), and pass through the locking opening (59) in order to block an axial displacement of the injection loading part (3).

2. The injection device (1) according to claim 1, characterized in that the injection device (1) has the drive (7) of the proximal part (5) as the only drive (7), the drive (7) acting in particular on a piston rod (41) to axially displace the piston rod (41), the injection device (1) preferably being configured in such a way that at least one other mechanical function of the injection device (1) is additionally realized by the displacement of the piston rod (41).

3. The injection device (1) according to claim 1, characterized in that the injection device (1) is designed as a pen or as an auto-injector.

4. The injection device (1) according to claim 1, characterized in that the distal part (13) is detachably connected to the proximal part (5).

5. The injection device (1) according to claim 1, characterized in that the screen (15) is rigid on the distal part (13), and is preferably formed by the distal part (13).

6. The injection device (1) according to claim 1, characterized in that a spring device (43) is arranged in the distal part (13), against which the injection loading part (3) rests, and against the spring force of which the injection loading part (3) can be displaced in the distal part (13) in the distal direction for performing an injection when the injection loading part (3) is arranged in the distal part (13).

7. The injection device (1) according to claim 1, characterized in that the locking part (47) has an axial passage opening (63) for a piston rod (41) assigned to the drive (7), the at least one locking element (53), in the first axial position, engaging in the passage opening (63), such that the passage opening (63) is blocked for the piston rod (41) and the locking part (47) can be displaced by the piston rod (41), wherein the locking elements (53), in the second axial position, clears the passage opening (63), such that the piston rod (41) can pass through the passage opening (63) and be displaced relative to the locking part (47).

8. The injection device (1) according to claim 1, characterized in that the screen (15) is held displaceably on the distal part (13).

9. The injection device (1) according to claim 1, characterized in that a distal end face (35) of the distal part (13) has a loading opening (39) through which the injection loading part (3) can be inserted into the distal part (13), wherein the injection loading part (3) can preferably be screwed into the distal part (13), and/or the injection loading part (3) can be arranged in an axially fixed manner in the distal part (13).

10. The injection device (1) according to claim 1, characterized in that the injection device (1) comprises the injection loading part (3), the injection loading part (3) has a packaging means receiving part (17) in which a primary packaging means (23) is held, a pharmaceutical substance being arranged in the primary packaging means (23).

11. An injection device (1) for injecting a pharmaceutical substance, comprising
a proximal part (5) which has a drive (7) to implement an injection, and having
a distal part (13) which is configured to accommodate an injection loading part (3), which has a packaging means receiving part (17) and a primary packaging means (23) which held in the packaging means receiving part (17) and in which a pharmaceutical substance is received, wherein the pharmaceutical substance can be injected from the injection loading part (3) when the injection loading part (3) is arranged in the distal part (13), wherein
the distal part (13) is designed in such a way that the injection loading part (3) can be inserted axially into the distal part (13), wherein
the injection device (1) has a screen (15) which is designed and arranged in such a way that an injection needle (25) of the injection loading part (3) is concealed from a user during use of the injection device (1), wherein
the distal part (13) has a screen locking mechanism (89) which is configured to block the screen (15) in a blocking position and to release it in a release position, wherein the screen locking mechanism (89) is configured to be unblocked when the injection loading part (3) is inserted into the distal part (13), and to be blocked by a piston rod (41) assigned to the drive (7), and wherein
the screen locking mechanism (89) has a rotary disk (91) which is arranged in the distal part (13) so that it can rotate about a longitudinal axis of the distal part (13) between the blocking position and the release position, wherein the rotary disk (91) has at least one recess passage (101) through which a blocking projection (93) of the screen (15) can be displaced in the release position, wherein the blocking projection (93), in the blocking position, strikes the rotary disk (91).

12. The injection device (1) according to claim 11, characterized in that the rotary disk (91) has
a) at least one driving surface (99) which is configured to work together with a driver (67) of the injection loading part (3), such that the rotary disk (91) is rotated from the blocking position into the release position when the injection loading part (3) is screwed into the distal part (13); and/or b) at least one runoff surface (103) on which an actuating structure (95) of the piston rod (41) can move in such a way that the rotary disk (91) is rotated from the release position into the blocking position when the piston rod (41) is displaced axially in a specific direction.

13. The injection device (1) according to claim 12, characterized in that the injection device (1) comprises the injection loading part (3), the injection loading part (3) has a packaging means receiving part (17) in which a primary packaging means (23) is held, a pharmaceutical substance being arranged in the primary packaging means (23), the injection loading part (3) has at least one driver (67) which is configured to work together with the at least one driving surface (99) of the rotary disk (91) of the distal part (13) in such a manner that the rotary disk (91) is rotated from the blocking position into the release position when the injection loading part (3) is screwed into the distal part (13).

14. The injection device (1) according to claim 13, characterized in that the packaging means receiving part (17) has a functional sleeve (19) and a retaining part (29), the primary packaging means (23) being accommodated in the functional sleeve (19), and the primary packaging means (23) being secured by the retaining part (29) in the functional sleeve (19).

15. The injection device (1) according to claim 14, characterized in that the injection loading part (3) has a needle protection part (21) which is detachably connected to the functional sleeve (19) and which conceals an injection needle (25) of the primary packaging means (23) when the needle protection part (21) is connected to the functional sleeve (19).

16. The injection device (1) according to claim 15, characterized in that the needle protection part (21) has an outer grip sleeve (31) and an elastic protective element (33) which is arranged inside the outer grip sleeve (31) in a manner allowing it to move together therewith, in which the injection needle (25) is accommodated when the needle protection part (21) is connected to the functional sleeve (19).

17. The injection device (1) according to claim 11, characterized in that the injection device (1) has an adjustable limit stop (77) for the screen (15), wherein the screen (15) preferably strikes the adjustable limit stop (77) in an exposed position in which an injection can be carried out.

* * * * *